(12) United States Patent
Zich et al.

(10) Patent No.: US 6,806,371 B2
(45) Date of Patent: Oct. 19, 2004

(54) PREPARATION OF SUBSTITUTED PYRIDINE N-OXIDE COMPOUNDS

(75) Inventors: Thomas Zich, Linz (AT); Wolfgang Schiek, Passau (DE); Markus Rössler, Linz (AT); Christian Seifter, Linz (AT)

(73) Assignee: DSM Fine Chemicals Austria Nfg GmbH & Co KG, Linz (AT)

( * ) Notice: Subject to any disclaimer, the term of this patent is extended or adjusted under 35 U.S.C. 154(b) by 0 days.

(21) Appl. No.: 10/674,524

(22) Filed: Oct. 1, 2003

(65) Prior Publication Data

US 2004/0063957 A1 Apr. 1, 2004

(30) Foreign Application Priority Data

Oct. 1, 2002 (AT) .......................... 1482/2002

(51) Int. Cl.$^7$ ............................ C07D 213/02

(52) U.S. Cl. .................. 546/301; 546/155; 546/345

(58) Field of Search ............... 546/301, 345, 546/155

(56) References Cited

U.S. PATENT DOCUMENTS 4,271,304 A * 6/1981 Edington et al. ........... 546/290
4,672,121 A * 6/1987 Nummy ...................... 546/290

\* cited by examiner

*Primary Examiner*—Bernard Dentz
(74) *Attorney, Agent, or Firm*—Wenderoth, L:ind & Ponack L.L.P.

(57) ABSTRACT

A process for preparing substituted pyridine N-oxide compounds of the formula

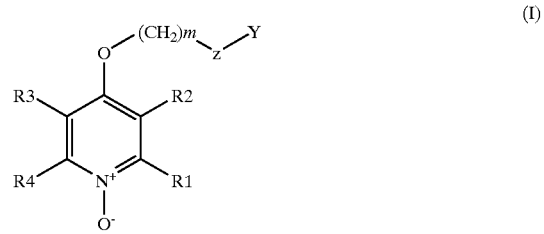

(I)

in which R1, R2, R3 and R4 are each H, a carboxyl group or a $C_1$–$C_{12}$-alkyl radical which may contain atoms from the group of N, O and S, or R1 and R2 and/or R3 and R4 together may each form an optionally substituted $C_4$–$C_{20}$-alkylene radical which may contain atoms from the group of N, O and S, A is benzyl or a $(CH_2)_m$ group where
m may be an integer from 1 to 12,
$Z_1$ and $Z_2$ are each independently O or S, and Y is H, a $C_1$–$C_{12}$-alkyl radical which may optionally contain atoms from the group of N, O and S, a $C_6$–$C_{20}$-aryl radical or a $C_5$–$C_{20}$-heterocycle, and the radicals may optionally be substituted,
or $Z_2$ and Y together form an optionally substituted ring or ring system, in which case the ring or ring system may contain atoms from the group of N, O and S, from the corresponding 4-halopyridine N-oxide of the formula

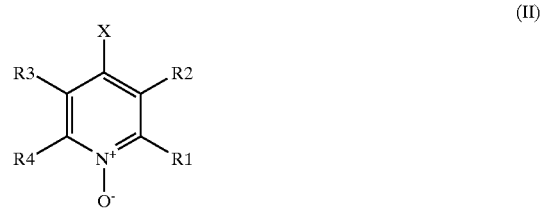

(II)

in which X is chlorine, bromine or iodine, by reacting the compound of the formula (II), in the presence of a phase transfer catalyst and of a base, with a compound of the formula $$HZ_1\text{-}A\text{-}Z_2\text{-}Y \tag{III}$$

in which $Z_1$, $Z_2$, A and Y are each as defined above, at a temperature up to the reflux temperature, to give the corresponding substituted pyridine N-oxide compound of the formula (I), and also a process for preparing the compound of the formula (II).

12 Claims, No Drawings

PREPARATION OF SUBSTITUTED PYRIDINE N-OXIDE COMPOUNDS

The invention relates to a process for preparing substituted pyridine N-oxide compounds by means of phase transfer catalysis.

Substituted pyridine N-oxide compounds are used in the pharmaceutical industry as intermediates in the preparation of medicaments which are effective, for example, against Helicobacter bacteria or, for instance, for treating and preventing stomach ulcers.

The preparation of substituted pyridine N-oxide compounds from the corresponding chloro derivatives is disclosed, for example, by EP-A-0 268 956, WO 98/28299 or WO 96/02534. However, the syntheses described in these references require the use of a strong base, for instance sodium hydride, in differing solvents such as DMF, DMSO or NMP, or the direct preparation of a sodium alkoxide from metallic sodium and alcohol. In addition, they usually achieve moderate yields.

According to this prior art, the preparation of the desired substituted pyridine N-oxide compounds is also possible without use of a solvent. This does not alleviate the above-mentioned disadvantages, especially the use of strong bases, the resulting danger potential and the necessary measures for safe handling of these substances, the necessity, if at all, then to use dry solvent, the formation of hydrogen gas, the deficient selectivity of the conversion, and also parameters which are often required such as high temperature or long reaction time.

EP 0 297 783 discloses the preparation of alkoxypyridine 1-oxide compounds from the corresponding nitro derivatives. In this preparation, the appropriate nitropyridine 1-oxide compounds are reacted with a simple alcohol or an alkoxide of the formula ROM in which M is H or an alkali metal, in the presence of a base and of a phase transfer catalyst.

However, the reaction of chloro derivatives with diols, mercapto alcohols, ether alcohols, thioether alcohols, dithiols or thioether thiols, which lead to the substituted pyridine N-oxide compounds disclosed by EP-A-0 268 956, WO 98/28299 or WO 96/02534, has hitherto been effected in a similar manner to the above-described process.

It is an object of the invention to modify the reaction in such a way that the strong bases used are replaced by a less expensive alternative which is neither combustible nor explosive, the use of the solvents which are difficult to recycle, such as DMF and DMSO, is avoided, and a reaction in good selectivity in at least comparable time and at comparable temperatures is achieved.

Unexpectedly, this object could be achieved by the use of phase transfer catalysts.

The present invention therefore provides a process for preparing substituted pyridine N-oxide compounds of the formula

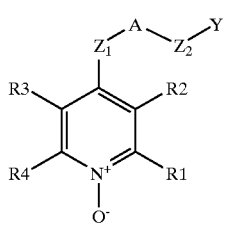

(I)

in which R1, R2, R3 and R4 are each independently H, a carboxyl group or a $C_1$–$C_{12}$-alkyl radical which optionally contain one or more atoms from the group of N, O and S, or R1 and R2 and/or R3 and R4 together may each form an optionally substituted $C_4$–$C_{20}$-alkylene radical which may contain one or more atoms from the group of N, O and S, A is benzyl or a $(CH_2)_m$ group where
m may be an integer from 1 to 12,
$Z_1$ and $Z_2$ are each independently O or S, and Y is H, a $C_1$–$C_{12}$-alkyl radical which may optionally contain one or more atoms from the group of N, O and S, a $C_6$–$C_{20}$-aryl radical or a $C_5$–$C_{20}$-heterocycle, and the radicals may optionally be substituted by halogen, $C_1$–$C_6$-alkyl, nitro, phenyl or tert-amine,
or $Z_2$ and Y together may form an optionally substituted ring or an optionally substituted ring system, and the ring or the ring system may contain one or more atoms from the group of N, O and S, from the corresponding 4-halopyridine N-oxide of the formula

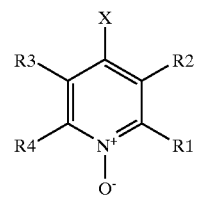

(II)

in which R1–R4 are each as defined above and X is chlorine, bromine or iodine, which comprises reacting the compound of the formula (II) in the presence of a phase transfer catalyst and of a base with a compound of the formula $$HZ_1\text{-}A\text{-}Z_2\text{-}Y$$ (III)

in which $Z_1$, $Z_2$, A and Y are each as defined above, at a temperature up to the reflux temperature, to give the corresponding substituted pyridine N-oxide compound of the formula (I).

According to the present invention, substituted pyridine N-oxide compounds of the formula (I) are prepared.

In formula (I), R1, R2, R3 and R4 are each independently H, a carboxyl group or a $C_1$–$C_{12}$-alkyl radical which may optionally contain one or more atoms from the group of N, O and S.

In this context, $C_1$–$C_{12}$-alkyl radicals are linear, branched or cyclic alkyl radicals, for instance methyl, ethyl, n-propyl, i-propyl, n-butyl, sec-butyl, tert-butyl, n-pentyl, hexyl, cyclohexyl, etc. The alkyl chain may contain one or more atoms from the group of N, S and O.

R1 and R2 and/or R3 and R4 may also together form an optionally substituted $C_4$–$C_{20}$-alkylene radical which may contain one or more atoms from the group of N, O and S. The alkylene radical may additionally, depending on the size of the ring formed, also have one or two double bonds.

R1, R2, R3 and R4 are preferably each independently H or $C_1$–$C_4$-alkyl, more preferably H or methyl.

A may either be benzyl or a $(CH_2)_m$ group where m is an integer from 1 to 12, preferably a number from 2 to 6. $Z_1$ and $Z_2$ may each independently be O or S, and Y may be H, a $C_1$–$C_{12}$-alkyl radical which may optionally contain one or more atoms from the group of N, O and S, a $C_6$–$C_{20}$-aryl radical or a $C_5$–$C_{20}$-heterocycle, and the radicals may optionally be substituted by halogen, $C_1$–$C_6$-alkyl, nitro, phenyl or tert-amine.

In this context, $C_6$–$C_{20}$-aryl refers, for example, to compounds such as phenyl, biphenyl, naphthyl, etc.

In this context, heterocycle refers to cyclic radicals which contain at least one S, O or N atom in the ring. These are, for example, furyl, pyridyl, pyrimidyl, thienyl, isothiazolyl, imidazolyl, tetrazolyl, pyrazinyl, benzofuranyl, benzothiophenyl, quinolyl, isoquinolyl, benzothienyl, isobenzofuryl, pyrazolyl, indolyl, isoindolyl, benzoimidazolyl, purinyl, carbazolyl, oxazolyl, thiazolyl, 1,2,4-thiadiazolyl, isoxazolyl, pyrrolyl, quinazolinyl, pyridazinyl, phthalazinyl, morpholinyl, etc.

$Z_2$ and Y may also together form an optionally substituted ring or an optionally substituted ring system, in which case the ring or the ring system may contain one or more atoms from the group of N, O and S. Examples thereof are 3-nitro[1,2]b-pyridazine, 4-methyl-thiazole, methyltriazole, imidazole, etc.

Preferably, Y is H, a $C_1$–$C_6$-alkyl radical which may contain one or two atoms from the group of O and S, a $C_6$–$C_{10}$-aryl or $C_5$–$C_{10}$-heterocycle radical, and the radicals may optionally be substituted by $C_1$–$C_4$-alkyl, halogen, nitro, tert-amine or phenyl.

Examples of compounds of the formula (I) which can be prepared by the process according to the invention are, for instance, 4-(2-benzyloxyethoxy)-2,3-dimethylpyridine N-oxide, 4-(3-methoxypropoxy)-2,3-dimethylpyridine N-oxide, 4-(2-hydroxyethoxy)-2,3-dimethylpyridine N-oxide, 4-(4-methoxybutoxy)-2-methylpyridine N-oxide, 4-(3-methoxypropoxy)-2-methylpyridine N-oxide, 4-(3-methoxy-propoxy)-2,3,5-dimethylpyridine N-oxide, 2,3-dimethyl-4-(3-hydroxypropylthio)pyridine N-oxide, 2,3-dimethyl-4-(2-hydroxyethylthio)pyridine N-oxide, 2,3-dimethyl-4-(3-hydroxypropylthio)pyridine N-oxide, 4,6-dimethyl-4-(3-hydroxypropylthio)pyridine N-oxide, etc.

The starting compound used is an appropriate 4-halopyridine N-oxide compound of the formula (II) in which R1–R4 are each as defined in formula (I) and X is chlorine, iodine or bromine.

Preferably, X is chlorine.

Suitable compounds of the formula (II) are, for example, 4-chloro-2-methylpyridine N-oxide, 4-chloro-2,3,5-trimethylpyridine N-oxide, 4-chloro-2,3,5,6-tetramethylpyridine N-oxide, 4-chloro-2,5-dimethylpyridine N-oxide, 4-bromo-3,5-dimethylpyridine N-oxide, etc.

The compound of the formula (II) can be prepared, for example, from the corresponding 4-nitropyridine N-oxide compound, for instance in a similar manner to EP 0 268 956 by reacting with acetyl chloride at −10° C. A further preparation variant is to heat with concentrated hydrochloric acid in an autoclave at 170° C., as described, for instance, in J. Med. Chem. 1998, 41, 1777.

The compound of the formula (II) can also be prepared by reacting the corresponding 4-nitropyridine N-oxide compound, in the presence of a phase transfer catalyst and in the presence of an acid, with an appropriate salt in an organic solvent.

This preparation variant is novel and therefore also forms part of the subject-matter of the present invention.

In this preparation variant, 4-nitropyridine N-oxide compounds of the formula

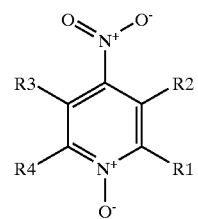

(IV)

in which R1 to R4 are as defined in formula (I) are reacted with a suitable, readily soluble salt, in the presence of a phase transfer catalyst and in the presence of an acid.

Suitable salts are, for example, alkali metal halides, for instance alkali metal chlorides, bromides or iodides.

The salt is used in a molar excess, based on the nitro compound. Preference is given to a molar ratio of compound of the formula (IV): salt of from 1:1.5 to 1:5, particular preference to from 1:2 to 1:4.

Suitable solvents are optionally halogenated hydrocarbons, for instance dichloromethane, toluene, etc.; ethers, for instance diisopropyl ether, etc., or acetonitrile.

According to the invention, the conversion is effected in the presence of a phase transfer catalyst. Useful phase transfer catalysts for the process according to the invention are quaternary ammonium salt compounds of the formula (V) $R_5R_6R_7R_8N^+A^-$ where the radicals $R_5$ to $R_8$ may each independently be $C_1$–$C_{20}$-alkyl, phenyl, arylalkyl or alkylaryl. The radicals may optionally be mono- or polysubstituted by functional groups, for example by amine or alcohol groups or by $C_1$–$C_4$-alkoxy. In this context, $C_1$–$C_{20}$-alkyl are linear, branched or cyclic radicals, for instance methyl, ethyl, n-propyl, i-propyl, n-butyl, sec-butyl, tert-butyl, n-pentyl, hexyl, cyclohexyl, octyl, undecyl, dodecyl, hexadecyl, etc.

In this context, arylalkyl is, for example, tolyl. Alkylaryl refers to alkyl groups which have an aryl substituent, for instance benzyl.

$R_5$ and $R_6$ may also be joined to give a 5- or 6-membered, heterocyclic system which contains at least one quaternized nitrogen atom and optionally further atoms from the group of N, S and O. An example thereof is 1-(ethylhexyl)-4-dimethylaminopyridine (EtHexDMAP).

Preference is given to compounds of the formula (V) in which $R_5$–$R_8$ are each independently a $C_1$–$C_{16}$-alkyl radical or benzyl radical.

$A^-$ in formula (V) is an anion which may be adapted as desired. Examples of suitable anions are, for instance, chloride, bromide, fluoride, iodide, hydroxide, hydrogensulfate, perchlorate, nitrate, acetate, benzoate, mesylate, etc.

Preferably, $A^-$ is chloride or bromide.

Examples of suitable compounds of the formula (V) are, for instance, tetraalkylammonium salts such as tetra-ethyl-, tetrapropyl-, tetrabutyl- to tetradodecyl-ammonium chlorides or bromides, tributylhexadecylammonium chloride or bromide, trioctylmethyl- (Aliquat 336), tributylmethyl-, tridecylmethylammonium chloride, bromides or hydrogensulfates, etc.; arylalkylammonium salts such as tetrabenzyl-, benzyltrimethyl-, benzyl-triethyl-, benzyltributylammonium chlorides or bromides, etc.;

arylammonium salts such as triphenylmethylammonium chloride, fluoride or bromide, N,N,N-trimethylanilinium bromide, N,N-diethyl-N-ethylanilinium hydrogensulfate, trimethylnaphthylammonium chloride, 5- and 6-membered heterocyclic compounds which bear at least one quaternized nitrogen atom in the ring, for example N-methylpyridinium chloride, N-hexylpyridinium iodide, 4-pyridyltrimethylammonium iodide, 1-methyl-1-azabicyclo[2.2.1]heptane bromide, N,N-dibutylmorpholinium chloride, N-ethylthiazolium chloride, N-butylpyrrolium chloride and other substances.

Phase transfer catalysts suitable for the process according to the invention are also the quaternary phosphonium salts corresponding to the above description, and also polyethers of cyclic or acyclic nature, such as PEGs and crown ethers, or tris-[2-(2-methoxyethoxy)ethyl]amine (TDA-1) and alkyl-substituted guanidinium salts.

Preferred phase transfer catalysts for the conversion of the nitro compound of the formula (IV) to the corresponding halo compound of the formula (II) are tetrabutylammonium salts, tributylhexadecylammonium salts, benzyltributylammonium salts, trioctylmethylammonium salts, tridecylmethylammonium salts, triethylmethylammonium salts, and also tributylmethylammonium salts or their mixtures.

Particular preference is given to the chlorides and bromides of the above-listed ammonium salts.

Suitable acids are organic or inorganic acids which are nonoxidizing under the reaction conditions, for instance HCl, HBr or glacial acetic acid.

The conversion is preferably effected at reflux temperature.

On completion of reaction, the appropriate compound of the formula (II) is isolated from the reaction mixture extractively and then used for the conversion to the desired end product of the formula (I).

The compound (II) is reacted with an alcohol or thiol of the formula (III). In formula (III), A, $Z_1$, $Z_2$ and Y are each as defined in formula (I).

Suitable alcohols or thiols of the formula (III) are therefore, for example, 3-methoxypropanol, 2-benzyloxyethanol, ethylene glycol, 3-(3-methoxypropoxy)propanol, 4-methoxybutanol, 4-ethoxybutanol, 3-methylthiopropanethiol, 3-hydroxymercaptan, ethanedithiol, etc.

The two starting compounds of the formula (II) and of the formula (III) are used in the process according to the invention in a molar ratio of from 1:1.1 to 1:10, preferably from 1:1.5 to 1:8. Excess alcohol or excess thiol may, if desired, be recycled on completion of reaction.

According to the invention, the conversion is effected in the presence of a phase transfer catalyst. Useful phase transfer catalysts for the process according to the invention are in turn quaternary ammonium salt compounds of the formula (V) $R_5R_6R_7R_8N^+A^-$ where the R5 to $R_8$ radicals and also $A^-$ are as defined before.

Preference is given in turn to compounds of the formula (V) in which $R_5$–$R_8$ are each independently a $C_1$–$C_{16}$-alkyl radical or benzyl, and $A^-$ is chloride or bromide.

Phase transfer catalysts suitable for the process according to the invention are also the quaternary phosphonium salts corresponding to the above description, and also polyethers of cyclic or acyclic nature, such as PEGs and crown ethers, or tris-[2-(2-methoxyethoxy)ethyl]amine (TDA-1) and alkyl-substituted guanidinium salts.

Preferred phase transfer catalysts for the reaction of the compound of the formula (II) with the compound of the formula (III) are tetrabutylammonium salts, tetrahexylammonium salts, benzyltributylammonium salts, trioctylmethylammonium salts, tridecylmethylammonium salts, and also methyltributylammonium salts or their mixtures.

Particular preference is given to the chlorides and bromides of the above-listed ammonium salts.

The amount of catalyst required for the process according to the invention is between 0.1 and 30 mol %, based on the compound of the formula (II), preferably between 0.25 and 25 mol % and more preferably between 0.5 and 15 mol %.

The reaction according to the invention additionally takes place in the presence of a base. Suitable bases are solid or dissolved alkali metal hydroxides such as NaOH and KOH, alkali metal carbonates such as $K_2CO_3$, alkali metal hydrogen carbonates such as sodium hydrogencarbonate, and also mixtures thereof.

The base is used in excess, based on the compound of the formula (II).

Optionally, the conversion can also be effected in a solvent which is base-stable under the reaction conditions.

The reaction is carried out at reaction temperatures up to the reflux temperature, although preference is given to temperatures of from 60 to 100° C.

The reaction time is preferably between 1 h and 24 h, more preferably from 4 to 10 h. Longer reaction times are also possible if desired.

In the process according to the invention, preference is given to adding the alcohol or the thiol of the formula (III) to a mixture of compound of the formula (II) and phase transfer catalyst. This solution is then admixed with the base and heated with stirring to the desired reaction temperature.

On completion of reaction, the reaction mixture is filtered, for example through a glass frit, the organic phase is removed and the aqueous phase, optionally after diluting with water, is extracted with a suitable extractant, for instance with dichloromethane or any solvent used. The filter cake is washed with the solvent used for extraction and the organic phases are combined and washed with water. Finally, the solvent or extractant is removed.

The present invention further provides the overall process for preparing the substituted pyridine N-oxide compounds of the formula (I), which starts from the compound of the formula (IV).

The process according to the invention and the overall process provide the desired substituted pyridine N-oxide compounds in high selectivity, high yield and high purity.

EXAMPLE 1

397.8 g (4.41 mol) of 3-methoxypropanol were added to 95 g (0.6 mol) of 4-chloro-2,3-dimethylpyridine N-oxide and 17 g (0.06 mol) of tributylmethylammonium bromide. 101.4 ml of 50% NaOH were added dropwise to the clear solution. The reaction mixture was heated to 100° C. and stirred at this temperature for 8 h. The reaction mixture was filtered through a G3 glass frit. Subsequently, the organic phase was removed and the aqueous phase diluted with water and extracted repeatedly with dichloromethane. The filter cake was washed with dichloromethane and the organic phases were combined and washed with water. After removal of the solvent, 101.8 g (84.6%) of a brown oil remained which had a content of 96.8% of 4-(3-methoxypropoxy)-2,3-dimethylpyridine N-oxide.

EXAMPLE 2

83.0 g (0.49 mol) of 4-nitro-2,3-dimethylpyridine N-oxide and 90 g (1.54 mol) of NaCl were admixed with 1350 ml of $CH_3CN$, 180 ml of aq. HCl (36%) and 16.6 g of benzyltributylammonium chloride, and the resulting suspension was boiled under reflux with stirring for 12 h. The resulting reaction mixture was adjusted to pH=9 using 350 ml of 20% NaOH, wherefor the existing precipitate largely dissolved. The organic phase was separated off, water was added to the aqueous phase until the precipitate had completely dissolved, and it was subsequently extracted using dichloromethane. The organic phases were combined and the solvent was removed under reduced pressure. 76.6 g (98.5%) of 4-chloro-2,3-dimethylpyridine N-oxide were obtained.

What is claimed is:

1. A process for preparing substituted pyridine N-oxide compounds of the formula

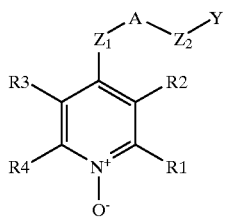

(I)

in which R1, R2, R3 and R4 are each independently H, a carboxyl group or a $C_1$–$C_{12}$-alkyl radical which may optionally contain one or more atoms from the group of N, O and S, or R1 and R2 and/or R3 and R4 together may each form an optionally substituted $C_4$–$C_{20}$-alkylene radical which may contain one or more atoms from the group of N, O and S, A is benzyl or a $(CH_2)_m$ group where m may be an integer from 1 to 12, $Z_1$ and $Z_2$ are each independently O or S, and Y is H, a $C_1$–$C_{12}$-alkyl radical which may optionally contain one or more atoms from the group of N, O and S, a $C_6$–$C_{20}$-aryl radical or a $C_5$–$C_{20}$-heterocycle, and the radicals may optionally be substituted by halogen, $C_1$–$C_6$-alkyl, nitro, phenyl or tert-amine, or $Z_2$ and Y together may form an optionally substituted ring or an optionally substituted ring system, and the ring or the ring system may contain one or more atoms from the group of N, O and S, from the corresponding 4-halopyridine N-oxide of the formula

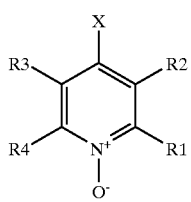

(II)

in which R1–R4 are each as defined above and X is chlorine, bromine or iodine, which comprises reacting the compound of the formula (II) in the presence of a phase transfer catalyst and of a base with a compound of the formula

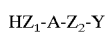

$HZ_1$-A-$Z_2$-Y (III)

in which $Z_1$, $Z_2$, A and Y are each as defined above, at a temperature up to the reflux temperature, to give the corresponding substituted pyridine N-oxide compound of the formula (I).

2. The process as claimed in claim 1, wherein compounds of the formula (I) are prepared in which R1, R2, R3 and R4 are each independently H or $C_1$–$C_4$-alkyl, A is benzyl or a $(CH_2)_m$ group where m is a number from 2 to 6, $Z_1$ and $Z_2$ may each independently be O or S, and Y is H, a $C_1$–$C_6$-alkyl radical which may contain one or two atoms from the group of O and S, a $C_6$–$C_{10}$-aryl or $C_5$–$C_{10}$-heterocycle radical, and the radicals may optionally be substituted by $C_1$–$C_4$-alkyl, halogen, nitro, tert-amine or phenyl.

3. The process as claimed in claim 1, wherein the compounds of the formula (II) and of the formula (III) are used in a molar ratio of from 1:1.1 to 1:10.

4. The process as claimed in claim 1, wherein the phase transfer catalyst used is an ammonium salt compound of the formula (V) $R_5R_6R_7R_8N^+A^-$ in which the $R_5$ to $R_8$ radicals may each independently be $C_1$–$C_{20}$-alkyl, phenyl, arylalkyl or alkylaryl, and the radicals may optionally be mono- or polysubstituted by functional groups, and $A^-$ is an anion from the group of chloride, bromide, fluoride, iodide, hydroxide, hydrogensulfate, perchlorate, nitrate, acetate, benzoate or mesylate, or is a corresponding quaternary phosphonium salt, polyether of cyclic or acyclic nature, or else an alkyl-substituted guanidinium salt.

5. The process as claimed in claim 1, wherein the phase transfer catalyst used is an ammonium salt compound of the formula (V) $R_5R_6R_7R_8N^+A^-$ in which the $R_5$ to $R_8$ radicals are each independently a $C_1$–$C_{16}$-alkyl radical or a benzyl radical, and $A^-$ is a chloride or bromide.

6. The process as claimed in claim 1, wherein the phase transfer catalyst is used in an amount of from 0.1 to 30 mol %, based on the compound of the formula (II).

7. A process for preparing a 4-halopyridine N-oxide compound of the formula (II)

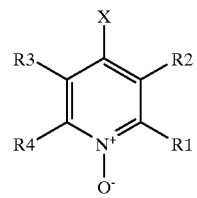

(II)

in which R1, R2, R3 and R4 are each independently H, a carboxyl group or a $C_1$–$C_{12}$-alkyl radical which may optionally contain one or more atoms from the group of N, O and S, or R1 and R2 and/or R3 and R4 together may each form an optionally substituted $C_4$–$C_{20}$-alkylene radical which may contain one or more atoms from the group of N, O and S, and X is chlorine, bromine or iodine, which comprises reacting a 4-nitropyridine N-oxide compound of the formula

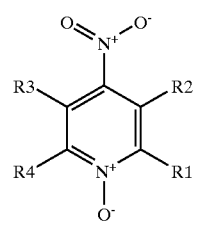

(IV)

in which R1 to R4 are as defined in formula (II), in the presence of a phase transfer catalyst and in the presence of an acid, with an alkali metal halide to give the corresponding compounds of the formula (II).

8. The process as claimed in claim 7, wherein the phase transfer catalyst used in the conversion of the compound of the formula (IV) to the compound of the formula (II) is an ammonium salt compound of the formula (V) $R_5R_6R_7R_8N^+ A^-$ in which the $R_5$ to $R_8$ radicals may each independently be $C_1$–$C_{20}$-alkyl, phenyl, arylalkyl or alkylaryl, and the radicals may optionally be mono- or polysubstituted by functional groups, and $A^-$ is an anion from the group of chloride, bromide, fluoride, iodide, hydroxide, hydrogensulfate, perchlorate, nitrate, acetate, benzoate or mesylate, or a corresponding quaternary phosphonium salt, polyether of cyclic or acyclic nature, or else an alkyl-substituted guanidinium salt.

9. The process as claimed in claim 7, wherein the phase transfer catalyst used is an ammonium salt compound of the formula (V) $R_5R_6R_7R_8N^+A^-$ in which the $R_5$ to $R_8$ radicals are each independently a $C_1$–$C_{16}$-alkyl radical or a benzyl radical, and $A^-$ is a chloride or bromide.

10. The process as claimed in claim 7, wherein the acid used in the conversion of the compound of the formula (IV) to the compound of the formula (II) is HCl, HBr or glacial acetic acid.

11. The process as claimed in claim 7, wherein the conversion of the compound of the formula (IV) to the compound of the formula (II) is carried out in a solvent from the group of the optionally halogenated hydrocarbons, ethers and nitriles.

12. A process for preparing substituted pyridine N-oxide compounds of the formula

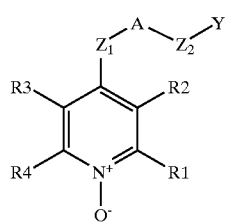

(I)

in which R1, R2, R3 and R4 are each independently H, a carboxyl group or a $C_1$–$C_{12}$-alkyl radical which may optionally contain one or more atoms from the group of N, O and S, or R1 and R2 and/or R3 and R4 together may each form an optionally substituted $C_4$–$C_{20}$-alkylene radical which may contain one or more atoms from the group of N, O and S, A is benzyl or a $(CH_2)_m$ group where m may be an integer from 1 to 12, $Z_1$ and $Z_2$ are each independently O or S, and Y is H, a $C_1$–$C_{12}$-alkyl radical which may optionally contain one or more atoms from the group of N, O and S, a $C_6$–$C_{20}$-aryl radical or a $C_5$–$C_{20}$-heterocycle, and the radicals may optionally be substituted by halogen, $C_1$–$C_6$-alkyl, nitro, phenyl or tert-amine, or $Z_2$ and Y together may form an optionally substituted ring or an optionally substituted ring system, and the ring or the ring system may contain one or more atoms from the group of N, O and S, which comprises reacting a 4-nitropyridine N-oxide compound of the formula

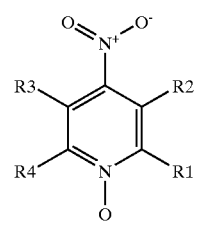

(IV)

in which R1 to R4 are each as defined in formula (I), in the presence of a phase transfer catalyst and in the presence of an acid, with an alkali metal halide to give the corresponding compounds of the formula

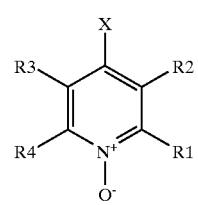

(II)

in which R1 to R4 are each as defined in formula (I) and X is chlorine, bromine or iodine, and then afterwards, after isolating it from the reaction mixture, reacting the compound of the formula (II), in the presence of a phase transfer catalyst and of a base, with a compound of the formula $HZ_1$-A-$Z_2$-Y (III)

in which $Z_1$, $Z_2$, A and Y are each as defined above, at a temperature up to the reflux temperature, to give the corresponding substituted pyridine N-oxide compound of the formula (I).

* * * * *